United States Patent
Zurlo et al.

(10) Patent No.: US 12,037,360 B2
(45) Date of Patent: *Jul. 16, 2024

(54) COMPOSITIONS AND METHODS FOR ISOLATING PROTEINS

(71) Applicant: Plasma Technologies, LLC, Charleston, SC (US)

(72) Inventors: Eugene Zurlo, Charleston, SC (US); Dennis Curtin, Charleston, SC (US); Klaus Peter Radtke, Apex, NC (US); Ryan Dorfman, Essex, VT (US); Matthew Whelihan, Colchester, VT (US)

(73) Assignee: Plasma Technologies, LLC

( * ) Notice: Subject to any disclaimer, the term of this patent is extended or adjusted under 35 U.S.C. 154(b) by 0 days.

This patent is subject to a terminal disclaimer.

(21) Appl. No.: 17/560,219

(22) Filed: Dec. 22, 2021

(65) Prior Publication Data

US 2023/0129803 A1    Apr. 27, 2023

Related U.S. Application Data

(60) Provisional application No. 63/272,605, filed on Oct. 27, 2021.

(51) Int. Cl.
   *C07K 1/22* (2006.01)
   *B01D 15/36* (2006.01)
   (Continued)

(52) U.S. Cl.
   CPC .............. *C07K 1/22* (2013.01); *B01D 15/362* (2013.01); *B01D 15/363* (2013.01); *C07K 1/165* (2013.01); *C07K 1/18* (2013.01); *C07K 1/20* (2013.01)

(58) Field of Classification Search
   CPC .......... C07K 16/065; C07K 1/36; C07K 1/22; C07K 1/303; C07K 1/18
   See application file for complete search history.

(56) References Cited

U.S. PATENT DOCUMENTS

| | | | |
|---|---|---|---|
| 6,069,236 A | 5/2000 | Burnouf-Radosevich |
| 8,063,189 B2 | 11/2011 | Arunakumari |

(Continued)

FOREIGN PATENT DOCUMENTS

| | | |
|---|---|---|
| EP | 2639239 | 9/2017 |
| WO | 2011149472 | 12/2011 |

(Continued)

OTHER PUBLICATIONS

International Search Report dated Apr. 15, 2022 from related PCT application No. PCT/US2021/065017. 8 pages.

(Continued)

*Primary Examiner* — Shafiqul Haq
(74) *Attorney, Agent, or Firm* — Fish IP Law, LLP

(57) ABSTRACT

Systems and methods are described in which proteins are isolated from complex solution using successive chromatographic separations that retain the protein of interest in the flow-through. At least one of the chromatography media used is selected to be capable of interacting with both contaminants and the protein of interest, however capacity of this media is selected such that the protein of interest is displaced and remains in the flow-through.

12 Claims, 3 Drawing Sheets

(51) Int. Cl.
    *C07K 1/16*    (2006.01)
    *C07K 1/18*    (2006.01)
    *C07K 1/20*    (2006.01)

(56) References Cited

U.S. PATENT DOCUMENTS

| | | |
|---|---|---|
| 9,096,648 B2 | 8/2015 | Bian |
| 9,556,253 B2 | 1/2017 | Nuvula |
| 10,815,270 B1 | 10/2020 | Zurlo |
| 2013/0184439 A1 | 7/2013 | Spitali |
| 2016/0272674 A1 | 9/2016 | Althouse |
| 2020/0283472 A1 | 9/2020 | Karur |
| 2022/0204556 A1* | 6/2022 | Zurlo .................. C07K 16/065 |

FOREIGN PATENT DOCUMENTS

| | | | |
|---|---|---|---|
| WO | 2012030512 | 3/2012 | |
| WO | WO-2016005016 A1 * | 1/2016 | ......... B01D 15/1871 |

OTHER PUBLICATIONS

Gotteschalk, Uwe. "Bioseparation in Antibody Manufacturing: The Good, the Bad and The Ugly." Biotechnol. Prog. 2008, 24, 496-503. 8 pages.

Matulis, Daumantas. "Selectrive Precipitation of Proteins," Department of Biothermodynamics and Drug Design. Curr. Protoc. Protein Sci 83:4.5.1-4.37. 37 pages.

* cited by examiner

US 12,037,360 B2

COMPOSITIONS AND METHODS FOR ISOLATING PROTEINS

This application claims the benefit of U.S. Provisional Patent Application No. 63/272,605, filed Oct. 27, 2021. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is the isolation of proteins from heterogeneous protein solutions.

BACKGROUND

The background description includes information that may be useful in understanding the present invention. It is not an admission that any of the information provided herein is prior art or relevant to the presently claimed invention, or that any publication specifically or implicitly referenced is prior art.

Isolation of proteins at high purity generally requires the use of multiple purification steps, at least one of which is a chromatography step. Chromatography can be performed in either positive selection mode (in which the protein of interest binds to and is later eluted from the chromatography media following a washing step) or negative selection mode (in which the protein of interest appears in a flow-through fraction).

Chromatography that utilizes positive selection is generally used to provide proteins of high purity (e.g., exceeding 80% purity by weight). For example, affinity chromatography media is typically used to bind a protein of interest from a sample that includes contaminants to the affinity media. Following washing steps to remove contaminants, the protein of interest is then eluted from the affinity media in an elution buffer at high purity, for example by applying a low pH buffer. Unfortunately, such elution is generally incomplete, and the elution buffer used can result in denaturation of the protein being isolated.

Methods for isolation of a protein at high purity typically utilize multiple chromatography steps. For example, in a typical isolation process for immunoglobulin G (IgG) an anion exchange chromatography media is used in negative selection mode, with IgG appearing in the flow-through and some contaminants binding to the anion exchange media. The anion exchange media is used in conjunction with a cation exchange chromatography media that is used in positive selection mode, which binds the IgG and allows remaining contaminants pass in the flow-through. Following a wash step, the bound IgG is eluted at high purity using a buffer with high ionic strength. This elution step, however, is generally incomplete.

In using such a conventional purification strategy for a therapeutic protein product the loss of target protein is particularly consequential when applied to a relatively pure solution with low concentrations of contaminants (which nevertheless need to be removed due to their adverse side effects at even femtomolar concentrations). For example, low concentrations of coagulation proteins, or host cell proteins often need to be removed due to their potential for severe adverse events.

Unfortunately, binding to and subsequent elution from chromatography media inevitably leads to significant loss (e.g., up to 10% or more) of the bound protein. In addition, while processes that utilize positive selection are useful on a small scale, application, process complexity, time requirements, and material limitations (in terms of both costs and physical limits of the chromatography media) render them unsuitable for large scale protein isolation processes (which can involve processing of 8,000 liters or more of material).

Thus, there is still a need for rapid, efficient, and scalable methods for isolation of proteins at high yield and purity.

SUMMARY OF THE INVENTION

The inventive subject matter provides systems and methods in which proteins are isolated from a complex solution using one or more chromatographic separations that retain the protein of interest in the flow-through. At least one of the chromatography media used is selected to be capable of interacting with both contaminants and the protein of interest, however capacity of this media is selected such that the protein on interest is displaced and remains in the flow-through.

One embodiment of the inventive concept is a method for isolating a protein from a solution by obtaining a solution containing the protein of interest, a first contaminant, and a second contaminant and applying the solution to first chromatography media (e.g., an ion exchange media, an affinity media, a hydrophobic interaction media, or a mixed mode media) that binds the first contaminant. This generates a first flow-through that includes the protein and the second contaminant, which is applied to a second chromatography media (e.g., an ion exchange media, an affinity media, a hydrophobic interaction media, or a mixed mode media) selected to bind the second contaminant and to bind the protein. The protein of interest is found in a second flow-through from this second chromatography step. In a preferred embodiment the first and second chromatography media are ion exchange media having opposing charges. Capacity of this second chromatography media is selected so that less than 10% 3% of the protein of interest present in the first flow-through is lost in this second chromatography step. The solution containing the protein of interest can be a product of a preceding isolation step. Loss of the protein of interest in such a method can be less than 30% of the content of the protein in the starting solution. In a preferred embodiment the second chromatography media binds the second contaminant with a higher affinity than it does the protein of interest.

Optimization of the capacity of the second chromatography media can be performed by observing breakthrough of contaminants. For example, capacity of the second chromatography media can be selected to exceed amount necessary to see breakthrough of the second contaminant of the solution by less than 10% to 50%. Overall, capacity of the second chromatography media used is greatly reduced compared to conventional procedures in which the protein of interest is bound and subsequently eluted.

Another embodiment of the inventive concept is a system for isolating a protein from a solution (e.g., a product of a previous isolation step), which includes a first separation module containing a first chromatography media (e.g., an ion exchange media, an affinity media, a hydrophobic interaction media, or a mixed mode media) selected to remove a first contaminant from the solution, wherein the first separation module has a first output that carries a first flow-through. This first flow-through includes the protein and at least a second contaminant. Such a system also includes a second separation module containing a second chromatography media (e.g., an ion exchange media, an affinity media, a hydrophobic interaction media, or a mixed mode media). In a preferred embodiment the first and second chromatography media are ion exchange media having opposing charges. This second chromatography media is selected to bind the protein and the second contaminant. The second separation module has a second output carrying a flow-through that includes the protein. The second separation module includes an amount of the second chromatography media that is selected so that content of the protein (e.g., less than 30%, less than 25%, less than 20%, less than 15%, less than 10%, less than 5%, less than 3%, or less than 1%) in the solution is lost on passage through the second separation module. In some embodiments the second chromatography media is a filter.

Various objects, features, aspects and advantages of the inventive subject matter will become more apparent from the following detailed description of preferred embodiments.

DETAILED DESCRIPTION

The Inventors have developed a simple and scalable process that can isolate a protein of interest at high yield (e.g., greater than 60% of protein content of the starting material) and high purity (e.g., 70%, 75%, 80%, 85%, 90%, 95%, 98%, 99%, by weight or greater). These methods are particularly useful in isolation of a protein of interest from a solution that includes one or more contaminants that have chromatographic behavior that is similar to that of the protein of interest (e.g., binding to the same chromatography media).

Methods of the inventive concept utilize a chromatography media that has an affinity for both the protein that is to be isolated (i.e., the protein of interest) and one or more contaminants that are present in solution with the protein of interest. The chromatography media can be selected to have a higher affinity (i.e., interact more strongly) with one or more the contaminants than the protein of interest. The capacity of the chromatography media used is calculated on the basis of the contaminant content of the solution containing the protein of interest, and is selected such that break-through of one or more contaminants does not occur to a significant extend (e.g., greater than 0.01%, 0.1%, 0.25%, 0.5%, 1%, 2%, 5%, or 10%) of the contaminant content of the solution being purified. It should be appreciated that such chromatography media capacity is a function of the nature of the chromatography media, the amount of media used, solution composition, solution pH, flow rate, etc., and is readily determined and/or optimized experimentally. Generally the capacity of chromatography media required is relatively small relative to prior art methods, and can advantageously be provided by a functionalized (e.g., charged) filter.

In practice Inventors have found that, despite using chromatography media having the ability to capture the protein of interest under the buffer conditions used, application of methods of the inventive concept permit recovery of in excess of 70%, 75%, 80%, 85%, 90%, 95%, 97%, or 99% of the total protein of interest applied to chromatography media in the flow-through fraction. Without wishing to be bound by theory, inventors believe that interaction of contaminants with the chromatography media effectively displaces the protein of interest. This permits highly efficient recovery of a protein of interest from contaminants having similar charge or other characteristics that would otherwise make them difficult to separate from one another. Purity of the recovered protein of interest can be from 80%, 85%, 90%, 95%, 98%, 99%, or higher (by weight).

Figure 1:
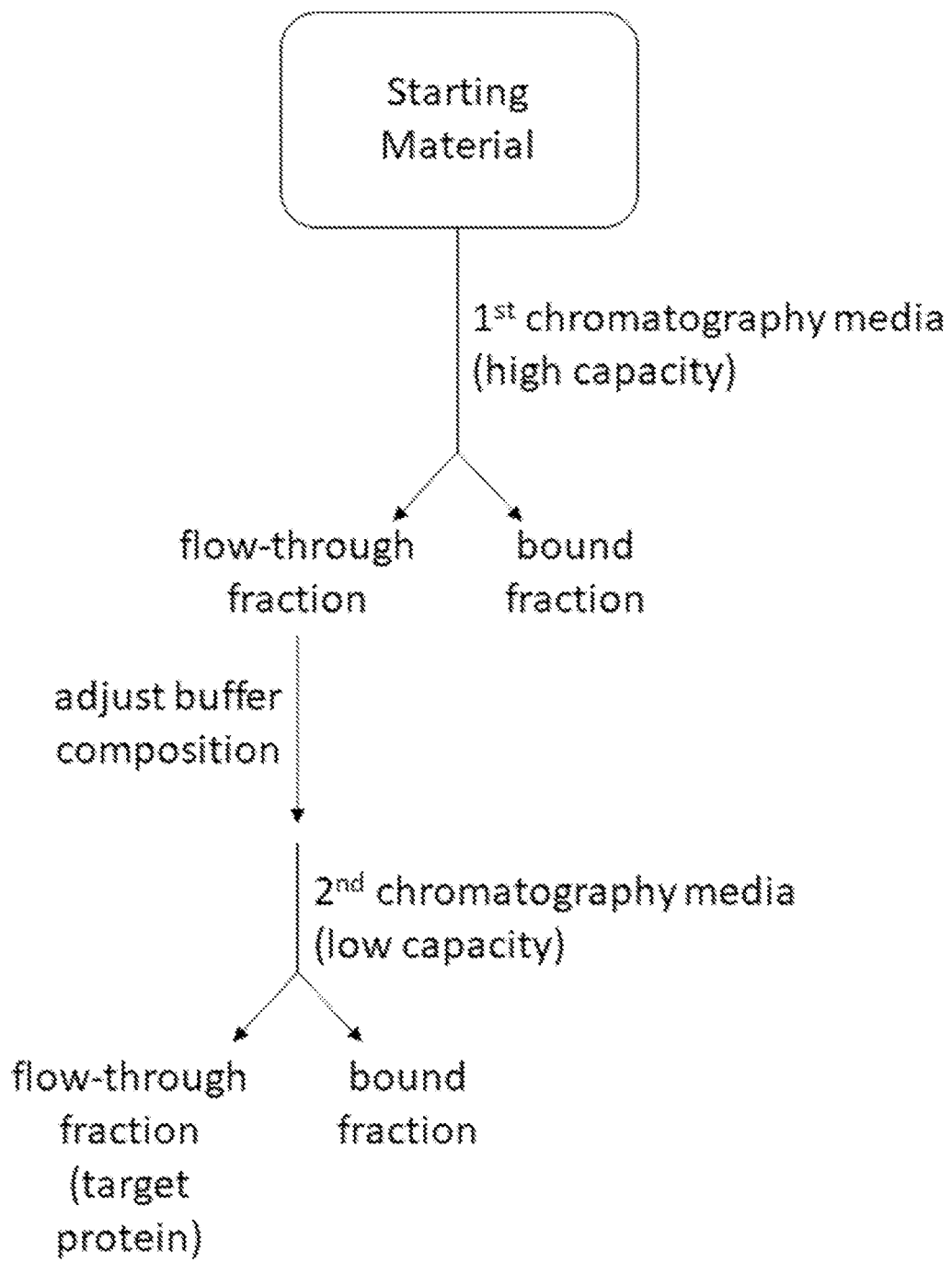
FIG. 1 schematically depicts an exemplary process of the inventive concept.

An example of a method of the inventive concept is shown schematically in FIG. 1. As shown, a solution containing the protein of interest and one or more contaminants is applied to a low capacity chromatography media. Buffer conditions (e.g., ionic strength, pH, temperature, etc.) can be adjusted prior to this application. Buffer conditions can be adjusted by any suitable means, for example addition or removal of one or more salt(s), addition of acid or base, etc. Suitable media include, but are not limited to, ion exchange media (e.g., DEAE, Q, S, or CN media), hydrophobic interaction media (e.g., propyl, butyl, or phenyl media), affinity media, or mixed-mode media. As noted above, the functionality of the chromatography media is selected to interact with both the protein of interest and one or more contaminants, however the capacity of the media is selected to match or slightly exceed (e.g., by 1%, 5%, 10%, 25%, 50%, 100%, 150%, or 200%) the capacity at which break-through of contaminant occurs. The protein of interest is subsequently collected at high yield and purity (as described above) in the flow-through fraction.

It should be appreciated that such an approach can greatly simplify processing of protein-containing solutions at large volumes (e.g., greater than 2 L, 10 L, 50 L, 250 L, 1000 L, 2500 L, 5000 L, 8000 L), as collection of the protein of interest does not require a separate set of elution steps and the process utilizes a minimal amount of chromatography media.

Some embodiments of the inventive concept can utilize two different chromatography media. One of these is selected to not interact with the protein of interest, and to bind a portion of the contaminating species present. The second chromatography media differs from the first chromatography media, and is selected and used under conditions in which it can bind with the protein of interest. Inventors have surprisingly found that such second chromatography media can be employed in negative selection mode (i.e., with the protein of interest being recovered in the flow-through from the media) to provide simple, efficient, and highly scalable methods.

In methods of the inventive concept the capacity of the second chromatography media (which is a function of both the chemistry of the chromatography media, the chromatography buffer, and amount used) is selected on the basis of its ability to bind contaminants remaining in the flow-through obtained from the first chromatography media. This capacity can, for example, be determined using break-through studies in which contaminants are applied to the second chromatography media until they appear in the flow-through (under defined conditions of buffer composition and flow rate). An amount of the second chromatography media sufficient to bind contaminant content at the desired scale can then be utilized in a combined process using both the first and second chromatography media. In some embodiments a small excess of capacity in this second chromatography media (e.g., 10%, 20%, 30%, 40%, 50%, 60%, 70%, 80%, 90%, or 100% excess) can be used.

Notably, the capacity of the second chromatography media is significantly less than that used in a conventional isolation method in which the protein of interest is bound and subsequently eluted (e.g., less than 10%, 5%, 1%, 0.5%, 0.25%, 0.1%). In some embodiments this permits use of functionalized (e.g., charged) filters having appropriate pendant groups in place of traditional bead or particle-based chromatographic media. This advantageously permits combining particle removal and chromatography steps.

Inventors have found that, despite having the ability to bind with the target protein, methods of the inventive concept typically recover the protein of interest at high yield (in excess of 60%, 70%, 75%, 80%, 85%, 90%, or 95%) in the flow-through from the second chromatography media. Without wishing to be bound by theory, the Inventors believe that utilization of a second chromatography step that utilizes a judiciously minimized amount of media capacity results in displacement of the protein of interest from the media by contaminants present in the first flow-through. This removes the need for an elution step, and results in increased yield. In addition, collection of the protein of interest in successive flow-through fractions from successive chromatography steps greatly simplifies the isolation process and transition from bench scale (up to about 2 L of starting material) to industrial scale (8,000 L or more of starting material).

One should appreciate that the disclosed techniques provide many advantageous technical effects including rapid provision of proteins from complex solutions at high purity and high yield at process scale.

The Inventors' process produces a more native protein since it is not bound and subsequently eluted from chromatography media using harsh conditions. This advantageously both enhances yield and reduces the chance of denaturation, while also simplifying the isolation process and greatly reducing processing time. As such it is distinct and different from (and much more cost effective than) current protein isolation processes that involve binding to and elution from chromatographic media, with improved protein stability, increased in vivo half-life, more rapid infusion rates, improved patient tolerance, and reduced immunogenicity of the protein therapeutic.

First and second chromatography media can be selected to have complementary binding characteristics. For example, the first chromatography media and the second chromatography media can be ion exchange media that have opposing charges under the separation conditions used (e.g., anion exchange followed by cation exchange, cation exchange followed by anion exchange). Although examples provided below cited the use of ion exchange media, Inventors contemplate that any chromatographic media having complementary binding characteristics can be paired in methods of the inventive concept. Suitable chromatography media include, but are not limited to, ion exchange media (e.g., DEAE, Q, CM, and/or S chromatography media), hydrophobic interaction chromatography media, affinity chromatography media, and mixed-mode chromatography media. For example, in some embodiments first and second chromatography media can be ion exchange media with opposing charges under separation conditions. Alternatively, in some embodiments ion exchange chromatography media or mixed-mode chromatography media can be paired with hydrophobic interaction chromatography media (with appropriate adjustments to ionic strength between chromatographic steps). In still other embodiments, an affinity chromatography media can be used as a first chromatographic media and ion exchange, hydrophobic interaction, or mixed-mode chromatographic media as the second chromatography media.

Preferred embodiments of the inventive concept can utilize both anion and cation exchange chromatography (which are relatively inexpensive and available in a wide variety of formats), where buffer conditions and column binding capacity are selected or optimized to provide the target protein (e.g., IgG) in the flow-through fraction of each chromatographic step. Towards this end an initial ion exchange step (e.g., anion exchange, cation exchange) can be performed using a high capacity ion exchange media that does not appreciably bind the protein of interest.

For example, in the isolation of IgG a large/high capacity anion exchange step can be performed, providing a flow-through fraction containing IgG (along with some contaminants) and retaining a bound fraction that includes a portion of the contaminating proteins present in the starting material. This flow-through fraction is then applied (in some embodiments following an adjustment of salt content and/or pH to adjust ionic strength/conductivity and or pH) to a small or low capacity cation exchange media.

The size of this small or low capacity cation exchange media is selected so that it is near or slightly (e.g., 1%, 2%, 5%, 10%, 20%, 30%, 40%, 50%) greater than the amount or capacity for breakthrough of a contaminating protein found in the flow-through of the anion exchange media (taking buffer conditions into account). Without wishing to be bound by theory, the Inventors believe that this permits contaminating proteins to displace IgG that may bind to the cation exchange media. Careful selection of the amount/capacity of the cation exchange media and/or buffer conditions provides efficient removal of contaminating protein while also providing high yields of IgG.

Figure 2:
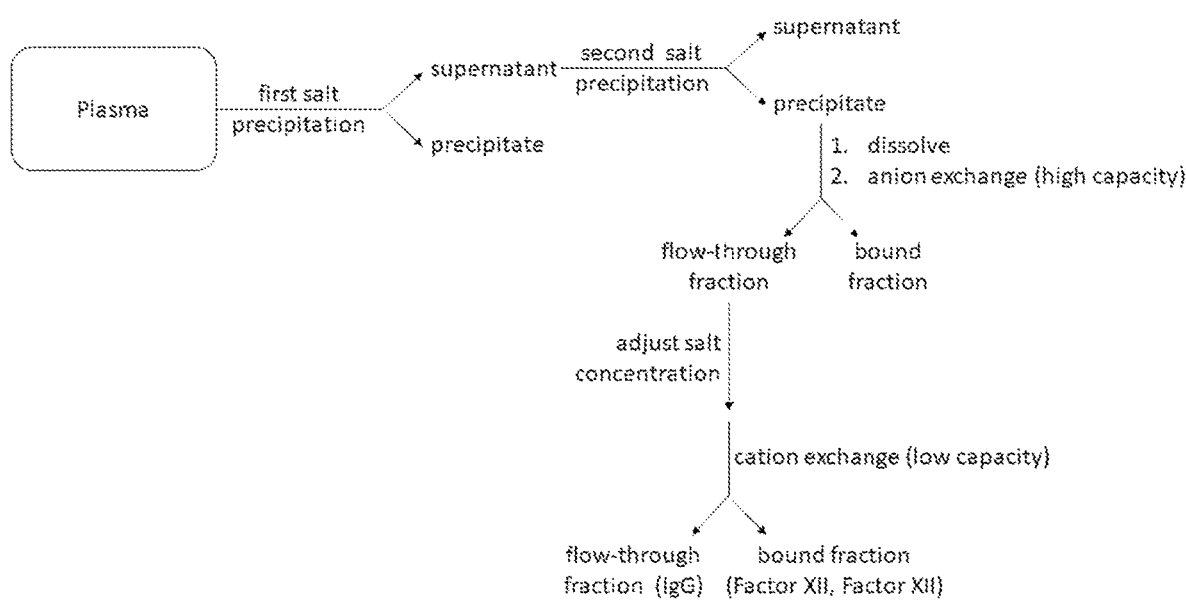
FIG. 2 schematically depicts an alternative exemplary process of the inventive concept.

An example of a process of the inventive concept is shown below in FIG. 2. It should be appreciated that in this context a starting material can be serum, plasma, cryo-poor plasma, cryo-poor plasma into which the cryoprecipitate has been re-dissolved, or a fraction (e.g., a supernatant or a dissolved precipitate) resulting from a precipitation step applied to such materials. Although blood proteins are of interest, a suitable starting material can be any solution containing a protein of interest (e.g., cell cultures, supernatants or lysates of cells from mammalian, bacterial, fungal, insect, or plant-based tissues or tissue cultures, solvated inclusion bodies, animal egg contents, milk, urine, or other body fluids, etc.). As shown, a starting material is applied to a high capacity first chromatography media selected to bind a portion of the contaminants and to not bind the protein of interest. The flow-through of this first chromatography step is directed (in some instances, after an adjustment in buffer composition and/or pH) to a second, different chromatographic media that is provided at low capacity. This second chromatography media can potentially bind the protein of interest as well as contaminants remaining in the first flow-through, but the capacity of the media is selected such that available binding sites are occupied by contaminants. Under these conditions the target protein is recovered in the flow-through from the second chromatography step at high yield (e.g., with less than 30%, 25%, 20%, 15%, 10%, 5%, 2.5%, or 1% of target protein present in the first flow-through lost).

Methods of the inventive concept are particularly suitable for isolation of therapeutic proteins, for example from blood and blood products. Examples of blood products include serum, plasma, cryoprecipitate, cryo-poor plasma, and cryo-poor plasma into which cryoprecipitate has been re-dissolved. Similarly, methods of the inventive concept are suitable for isolation of therapeutic proteins from products of conventional processes for protein isolation from blood products, including precipitation (e.g., with an organic solvent, an inorganic salt, an organic acid salt, and/or a hydrophilic polymer), chromatography, ultrafiltration, and/or diafiltration.

Methods of the inventive concept can also be applied to non-blood sources of therapeutic proteins. These include cell cultures, supernatants or lysates of cells from mammalian, bacterial, fungal, insect, or plant-based tissues or tissue cultures, solvated inclusion bodies, animal egg contents, milk, urine, or other body fluids, etc. products of cell-free protein synthesis, and products of protein conjugation processes.

Therapeutic proteins towards which methods of the inventive concept can be applied include, but are not limited to, albumin, alpha-one antitrypsin, immunoglobulins (e.g., IgG, IgM, IgA, IgY), clotting factors (e.g., Factor VIII, von Willebrand Factor), and host cell proteins (HSP).

Inventors have found methods of the inventive concept are particularly useful in the isolation of IgG from blood plasma, although application to other solutions containing IgG (e.g., cell culture media, cell lysates, other body fluids, etc.) is contemplated. Within the context of this application plasma is considered to include freshly collected plasma, refrigerated plasma, frozen plasma, cryo-poor plasma, and cryo-poor plasma into which the cryoprecipitate has been re-dissolved. Such plasma can, for example, be obtained as pooled material from commercial collection centers.

Figure 3:
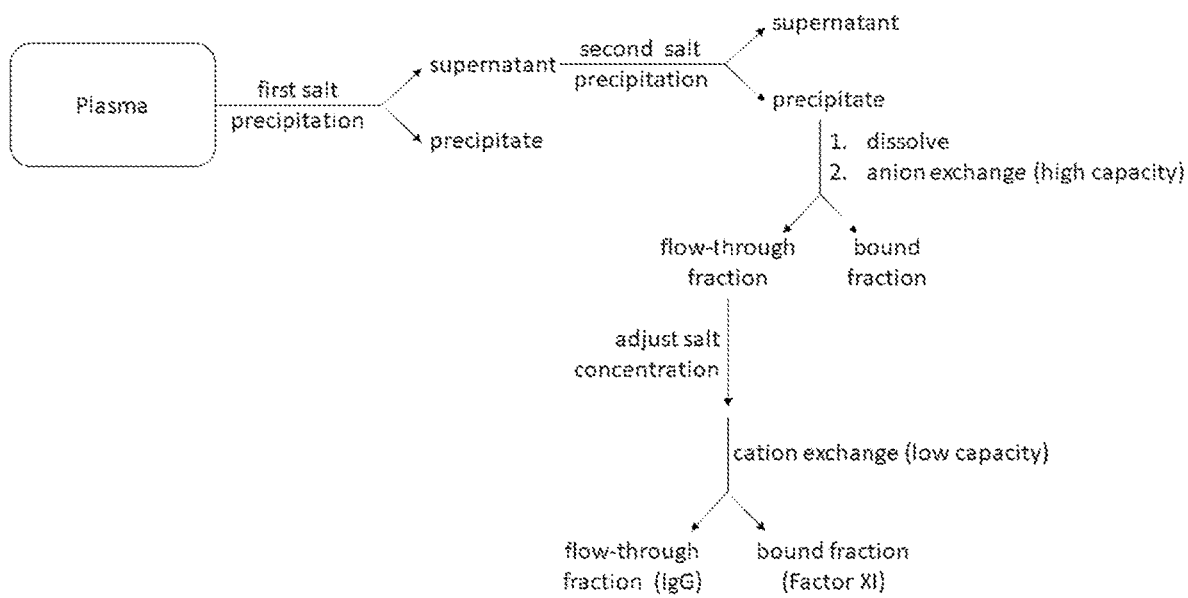
FIG. 3 schematically depicts an exemplary process of the inventive concept as applied to isolation of immunoglobulin G (IgG) from a blood product.

An example of a method of the inventive concept for isolation of IgG from plasma is shown in FIG. 3. The Inventors used two salt precipitation steps (i.e., about 11% in the first salt precipitation and about 26% in the second salt precipitation) to generate a protein solution from cryo poor plasma (CPP). This protein solution severed as starting material for the subsequent chromatography step and contained maximum IgG yield and minimized concentrations of unwanted proteins. As shown, the first precipitation step produces an IgG-rich supernatant, and the second precipitation step produces an IgG-rich precipitate or paste. This IgG-rich precipitate is dissolved (e.g., in water) prior to ion exchange steps. As noted below, in preferred embodiments a buffer exchange step (e.g., dialysis, diafiltration, ultrafiltration followed by dilution, size exclusion chromatography, etc.) is not performed prior to ion exchange steps.

Table 1

As shown in FIG. 3, using IgG as an example, the isolation process of the target protein in the inventive concept provides a first ion exchange step that can be performed using an anion exchange media (e.g., DEAE or Q chromatography media). In some embodiments a strong anion exchange media can be used that maintains a positive charge over a wide range of pH conditions (e.g., pH 1 to 14, pH 2 to 13, pH 3 to 12, pH 4 to 11). Chromatography media (e.g., anion exchange media as cited in this example) can be provided in any suitable form and/or on any suitable support (e.g., agarose, cross linked agarose, cellulose, polyacrylamide, polystyrene, glass, or combinations thereof) and in any suitable configuration (e.g., porous beads, non-porous beads, fibers, wools, filters, etc.).

As shown in FIG. 3, in an IgG process of the inventive concept IgG is recovered in the flow-through (i.e., unbound) fraction from the anion exchange media. This first flow-through fraction is subsequently applied to a small or low capacity cation exchange media (e.g., media that includes carboxylate or sulfonate groups) in which size/capacity has been selected such that contaminants (e.g., Factor XL activated Factor XI, Factor XII, activated Factor XII) are retained while IgG (which typically also binds to cation exchange media) passes through in the flow-through fraction (i.e., the second flow-through fraction). Typically, the capacity or size of the cation exchange media is selected to be at or slightly exceeding (e.g., by 1%, 2%, 5%, 10%, 15%, 20%, 25%, 30%, 50%, 75%, or 100%) its capacity for contaminants present in the first flow-through fraction. Without wishing to be bound by theory, Inventors believe that when a cation exchange media is so selected bound protein (e.g., IgG) is displaced by the contaminated protein and released into the second flow-through fraction, thereby increasing yield. In preferred embodiments loss of IgG in the cation exchange step is less than about 30%, 25%, 15%, 10%, 7.5%, 5%, 4%, 3%, 2%, or 1% of IgG content of the starting material.

Such second chromatography media (e.g., a cation exchange media in this example) can be provided on any suitable support (e.g., agarose, cross linked agarose, cellulose, polyacrylamide, polystyrene, glass, or combinations thereof) and in any suitable configuration (e.g., porous beads, non-porous beads, fibers, wools, filters, etc.). Inventors have found that the capacity of the cation exchange media utilized can be quite small, and in preferred embodiments can be provided by a filter with pendant cation exchange groups. This advantageously combines purification and clarification steps.

In some embodiments of the inventive concept the buffer composition and/or pH of the first flow-through fraction can be modified prior to application to the second chromatography media (e.g., the cation exchange media of this example) in order to optimize capacity and selectivity for contaminants. For example, buffer conditions can be selected or adjusted such that contaminants have a higher affinity for the second chromatography media than that of the target protein. In preferred embodiments of protein (IgG) isolation methods of the inventive concept salts can be added to increase the ionic strength or conductivity of the first flow-through fraction to fall within a desired range. Alternatively, the first flow-through can be diluted or subjected to buffer exchange (e.g., dialysis, diafiltration, etc.) prior to application to the second chromatography media.

In some embodiments the second flow-through fraction can be subjected to additional processing steps. Such additional processing steps can include nanofiltration for virus removal, such as filtration using a 0.02 µm pore membrane. Inventors have found that this effectively retains any remaining virus particles while minimizing yield losses.

In some embodiments the purified protein solution can be prepared for use by concentration and diafiltration in order to provide a drug product having a useful concentration in a pharmacologically compatible buffer that provides stability. For IgG, such a step can provide an IgG concentration of about 5% IgG (w/v) in a suitable formulation buffer (e.g., 0.2M glycine pH 4.2 to pH 6.5) with minimal losses. Concentration can be increased or otherwise adjusted using known methods.

Typical IgG yield results for an IgG isolation process of the inventive concept are shown in Table 1.

TABLE 1

| Sample | Concentration (A280/mL) | Volume (mL) | Total (A280) | Total IgG [A280] (mg) | IgG [Neph] (mg/mL) | Total IgG [Neph] (mg) | IgG Yield (%) |
|---|---|---|---|---|---|---|---|
| Cryo-poor Plasma | 44.41 | 2000 | 88820 | N/A | 8.25 | 16500 | 100.0 |
| First Supernatant | 35.62 | 2490 | 88693.8 | | 6.34 | 15786.6 | 95.7 |
| First Precipitate | N/A | 22.9 g | N/A | | | N/A | |
| Second Supernatant | 14.07 | 3850 | 54169.5 | | | | |
| Second Precipitate | N/A | 187 g | N/A | | | | |
| Dissolved Second Precipitate | 14.73 | 2000 | 29460 | N/A | 7.33 | 14660 | 88.8 |
| Post Depth Filter | 10.47 | 2570 | 26907.9 | N/A | 5.86 | 15060.2 | 91.3 |
| Post 0.2 μm Filter | 6.37 | 4284 | 27289.08 | N/A | 3.49 | 14951.16 | 90.6 |
| Anion Exchange Flow-Through | 2.63 | 5680 | 14938.4 | N/A | 2.3 | 13064 | 79.2 |
| Cation Exchange Flow-Through | 2.52 | 5930 | 14943.6 | 11495 | 2.13 | 12630.9 | 76.6 |
| Post Nano-Filtration | 2.24 | 6107 | 13679.68 | N/A | | N/A | |
| Final Product | 67.11 | 248 | 16643.28 | 12802 | N/A | N/A | 77.6 |
| Total Additive Loss from Sample Removal | | | | | | 0.96 | |

Total yield based on $A_{280}$ absorbance/initial nephelometry values corrected for sample removal.
Extinction Coefficient for IgG: 1.3

Test results obtained from the material shown in Table 1 (i.e., 44.94 mg/mL IgG) are shown in Table 2.

TABLE 2

| Test | | Result | | Pass/Fail | EP Standard |
|---|---|---|---|---|---|
| PKA | | 1.48 IU/mL | | Pass | <35 IU/mL |
| IgA | | 1.57 μg/mL | | N/A | "Not more than is stated on the product label" |
| IgM | | Not Detectable | | N/A | No EP standard |
| IgG subclass | | IgG 1   IgG 2 | IgG 3   IgG 4 | | Product should be representative of starting material |
| Starting Material | | 62   28 | 7   4 | | |
| Finished Product | | 62   30 | 7   1 | | |
| Fc function | | 119% | | Pass | >60% |
| ACA | | 0.83 CH50 U/mg | | Pass | ≤1.5 CH50 U/mg |
| NaPTT | | 219.5 sec | | Pass | >200 sec |
| FXIa (chromogenic) | | <0.04 mU/mL | | Pass | No EP standard |
| FXIa (eCAT/TGA) | | 0.79 mU/mL | | Pass | No EP standard (<1 mU/mL historically in prior art) |

In addition to remarkably low levels of Factor XI contamination, the Inventors have found that methods of the inventive concept provide surprisingly low levels of IgA contamination.

Methods of the inventive concept applied to IgG were found to provide robust and commercially scalable processes that consistently produce about a 72-78% yield of IgG from starting plasma in just 48 hours. The resulting product is >99% pure IgG product with 100% functionality.

It should be appreciated that additional proteins can be recovered from various intermediate product streams produced by methods of the inventive concept, for example the bound fraction from the first chromatography step, and/or the bound fraction from the second chromatography step. Such intermediate products can be treated by any suitable method (e.g., additional precipitation steps, affinity chromatography, size exclusion chromatography, hydrophobic interaction chromatography, ion exchange chromatography, and/or mixed mode chromatography) to facilitate isolation of additional non-IgG proteins from the starting material.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method for isolating immunoglobulin G (IgG) from a solution comprising:
    subjecting a blood product to salt precipitation to obtain a crude IgG solution comprising obtaining a solution comprising IgG, a first contaminant having an affinity for a pendant diethylaminoethyl (DEAE) or quaternary amine (Q) group, and a second contaminant having an affinity for a pendant carboxymethyl (CM) or sulfopropyl (SP) group;
    applying the solution to an anion exchange media comprising the pendant DEAE or Q group under a first buffer condition selected to bind the first contaminant and to not bind IgG, to generate a first flow-through comprising IgG and the second contaminant from the anion exchange media;
    applying the first flow-through to a cation exchange media comprising the pendant CM or SP group under a second buffer condition selected to bind both the second contaminant and IgG; and
    collecting a second flow-through comprising IgG and less than 10% of content of the second contaminant in the first flow-through from the cation exchange media,
    wherein capacity of the cation exchange media is selected such that less than 3% of IgG content of the first flow through is lost on passage through the cation exchange media.

2. The method of claim 1, wherein loss of IgG is less than 30% of IgG content of the solution.

3. The method of claim 1, wherein the cation exchange media binds the second contaminant at a first affinity and IgG at a second affinity, and wherein the first affinity is greater than the second affinity.

4. The method of claim 1, comprising selecting capacity of the cation exchange media to exceed breakthrough by content of the second contaminant of the solution by less than 50%.

5. The method of claim 1, comprising selecting capacity of the cation exchange media to exceed breakthrough by content of the second contaminant of the solution by less than 25%.

6. The method of one of claim 1, comprising selecting capacity of the cation exchange media to exceed breakthrough by content of the second contaminant of the solution by less than 10%.

7. The method of claim 1, wherein the cation exchange media is configured as a particle or bead.

8. The method of claim 1, wherein at least one of the anion exchange media and the cation exchange media is configured as a filter.

9. The method of claim 1, wherein the second flow-through comprises less than 0.8 mU/mL of Factor XI.

10. The method of claim 1, wherein the second flow-through comprises less than 1.6 µg/mL immunoglobulin A.

11. The method of claim 1, further comprising a step of eluting the first non-IgG blood protein from the anion exchange media.

12. The method of claim 1, further comprising a step of eluting the second non-blood protein from the cation exchange media.

* * * * *